US00PP08881P

United States Patent [19]

van Andel

[11] Patent Number: Plant 8,881

[45] Date of Patent: Sep. 6, 1994

[54] MINI-SPRAY CARNATION PLANT NAMED 'STAGILAC'

[75] Inventor: Jacob van Andel, Aalsmeer, Netherlands

[73] Assignee: Van Staaveren, B.V., Aalsmeer, Netherlands

[21] Appl. No.: 99,271

[22] Filed: Jul. 29, 1993

Related U.S. Application Data

[63] Continuation of Ser. No. 756,798, Sep. 9, 1991, abandoned.

[51] Int. Cl.[5] ..... A01H 5/00

[52] U.S. Cl. ..... Plt./70.2

[58] Field of Search ..... Plt. 70.2, 70.1, 70.6, Plt. 70.5

[56] References Cited

U.S. PATENT DOCUMENTS

PLT7849 3/1992 van Andel ..... PLT/70.2

*Primary Examiner*—Howard J. Locker

*Attorney, Agent, or Firm*—Tilton, Fallon, Lungmus & Chestnut

[57] ABSTRACT

A new variety of mini-spray carnation particularly distinguished by its recurrent profuse production of small flowers, the petals of which are white at the base and purple to the outer edge, and by the rapid growth rate of the plant which takes the form of a bush with moderate foliage.

1 Drawing Sheet

This application is a continuation of application Ser. No. 07/756,798 filed Sep. 9, 1991 (abandoned).

BACKGROUND OF THE NEW PLANT

This new variety of spray carnation cultivar originated as a sport of the variety Statropur (U.S. Plant Pat. No. 7,849), being grown at Aalsmeer, Holland. This new spray carnation is a sport of unknown causation. The sport was found as a branch of Statropur. Stagilac differs from the parental cultivar in its overall plant height, the color of its petals, and its fruit fertility. Listed below, in Table 1, is a comparison of Stagilac with Statropur and other known sports of Statropur. The other sports listed are subjects of copending applications. Serial numbers for these applications are provided for in the Table.

TABLE 1

| | STAGILAC | STATROPUR | STA-VIOLET |
|---|---|---|---|
| SERIAL NO.: | 08/099,271 | 07/611,504 | 08/098,842 |
| RELATED APPLI-CATIONS: | 08/099,271 is a Continuation of 07/756,798 Abandoned | — | 08/098,842 is a Continuation 07/770,403 Abandoned |
| PATENT NO.: | — | U.S. Plant Pat. No. 7,849 | — |
| PETAL BODY: | RHS 74-B | RHS 74-B | RHS 74-A |
| PETAL BASE: | RHS 155-D | White | RHS 155-D |
| REVERSE SIDE: | RHS 72-C | White | RHS 155-D |
| STIGMA: | RHS 155-D | White | RHS 155-D |
| STYLE: | RHS 155-D | White | RHS 155-D |
| HEIGHT: | 100–110 cm. (average) | 150 cm. (average) | 100–110 cm. (average) |
| DIS-COLORATION AFTER FULL BLOOM: | Slight | None | Slight |
| FERTILE FRUIT: | No | Yes | No |

| | STAGIBORD | STAGIROS |
|---|---|---|
| SERIAL NO.: | 08/100,073 | 08/099,780 |
| RELATED APPLICATIONS: | 08/100,073 is a Continuation of 07/770,401 Abandoned | 08/099,780 is a Continuation of 07/770,402 Abandoned |
| PATENT NO.: | — | — |

TABLE 1-continued

| | | |
|---|---|---|
| PETAL BODY: | RHS 57-B + RHS 57 A ("Mottled Portion") | RHS 73-A + RHS 73-D ("Mottled Portion") |
| PETAL BASE: | RHS 155-D | RHS 155-D |
| REVERSE SIDE: | RHS 62-A | RHS 73-D |
| STIGMA: | RHS 64-B | RHS 155-D |
| STYLE: | RHS 64-B | RHS 155-D |
| HEIGHT: | 100–120 cm. (average) | 100 cm. (average) |
| DISCOLORATION AFTER FULL BLOOM: | Slight | Slight |
| FERTILE FRUIT: | No | No |

Stagilac was discovered in 1988 and propagated by me with cuttings for testing and evaluation because of its unusual flower coloring which is white at the base and purple to the outer edge of each petal. Stagilac was asexually propagated at my nursery in Aalsmeer, Holland.

The initial propagation by cutting proved to be successful, and further propagation confirmed that the new variety retained all of the distinguishing characteristics of the original mutation and that these characteristics hold true from generation to generation and appear to be firmly fixed.

DESCRIPTION OF THE DRAWING

This new spray carnation cultivar is illustrated by the accompanying photographic drawing which, in full color, shows the distinguishing color characteristics and flower form of this plant, the color rendition being as nearly true as it is reasonably possible to obtain by conventional photographic procedures.

DESCRIPTION OF THE NEW PLANT

The following is a detailed description of my new spray carnation plant with color designations according to the R.H.S. Colour Chart of the Royal Horticultural Society of London, England.

THE PLANT

Origin: Sport.

Parentage:
*Sport parent.*—Statropur.
*Patent No.*—U.S. Plant Pat. No. 7,849.
Classification:
*Botanic.*—Dianthus hybrid.
*Commercial.*—Mini-spray Carnation.
Form: Erect bush having at least four stems emitted near the ground.
Height: About 100–110 cm.
Stem length: About 100 cm.
Branching character: The main stem has 7–8 side branches and each side branch has 2–4 branches and each of these branches has 1–2 branches.
Growth: Vigorous, upright and medium strength.
*Rate.*—Fast.
Foliage:
*Quantity.*—Medium.
*Number of leaves.*—22–26.
*Size of leaf.*—About 7–11 cm. long and 1–2 cm. wide.
*Leaf shape.*—Elliptical.
*Margin type.*—Straight, entire.
*Texture.*—Smooth.
*Color.*—Upper side — Green (RHS 137-A). Under side — Light Green (RHS 137-C).

THE BUD

Form: Cylindrical.
Size:
*Diameter.*—0.3 to 0.4 cm.
*Length.*—2 to 2.5 cm.
Rate of opening: Fast.
Color of petals:
*When sepals first divide.*—RHS 72-C.
*When petals begin to unfurl.*—RHS 72-C.
Calyx:
*Shape.*—Cylindrical. The calyx is formed out of 5 pointed sepals of about 5 mm. which are joined at the lower point and are sharply pointed at the apex.
*Size.*—2 to 2.5 cm. long and 0.3 cm wide.
*Aspect.*—Smooth.
*Splitting.*—None.
Flower stem:
*Length.*—80–110 cm.
*Character.*—Strong and erect.
*Color.*—Dark Green (RHS 137-C).

THE FLOWER

Blooming habit: Recurrent and profuse year round.
Flower size: Small.
*Diameter.*—3 to 3.5 cm.
*Depth.*—0.5 cm.
Borne: Cluster.
Shape:
*When bloom first opens.*—Flat.
*When bloom matures.*—Flat.
Petalage:
*Number of petals.*—5.
*Arrangement.*—Side by side around the pistil.
*Form.*—Fan shaped with deeply serrated edges.
*Margin type.*—Dentate.
*Texture.*—Soft.
*Appearance.*—Velvety.
*Color.*—Body — RHS 74-B. Base — RHS 155-D. Reverse side — RHS 72-C.
Fragrance: Weak.
Discoloration after full bloom: Slight.
Persistence: The petals hang on and dry and bloom stays upright.
Disease resistance: Good resistance to *Fusarium oxysporum* as observed at the Horticultural Experimental Station of Aalsmeer, Holland.
Lasting quality:
*On plant.*—21 days.
*As cut flower.*—15 days.

THE REPRODUCTIVE ORGANS

Stamens:
*Number.*—Usually about 10 (if present).
*Arrangement.*—Alternating short/long.
*Anthers.*—Size: 2 mm. The anthers are not always present. If the anthers are present, they are rudimentary. Color: Yellow.
*Filaments.*—Length: If present, 5 mm. The filaments are not continually present. If they are present, they are rudimentary. Color: White. Pollen: None.
Pistils:
*Number.*—1.
*Style.*—Length: 1.5 to 2 cm. Color: White.
Stigmas:
*Color.*—White.
Fruit:
*Fertility.*—The fruit is not fertile.
*Shape.*—Pear-shaped.

I claim:

1. A new and distinct miniature spray carnation plant, substantially as herein shown and described, characterized by its recurrent profuse production of small flowers, which are white at the base and purple to the outer edge.

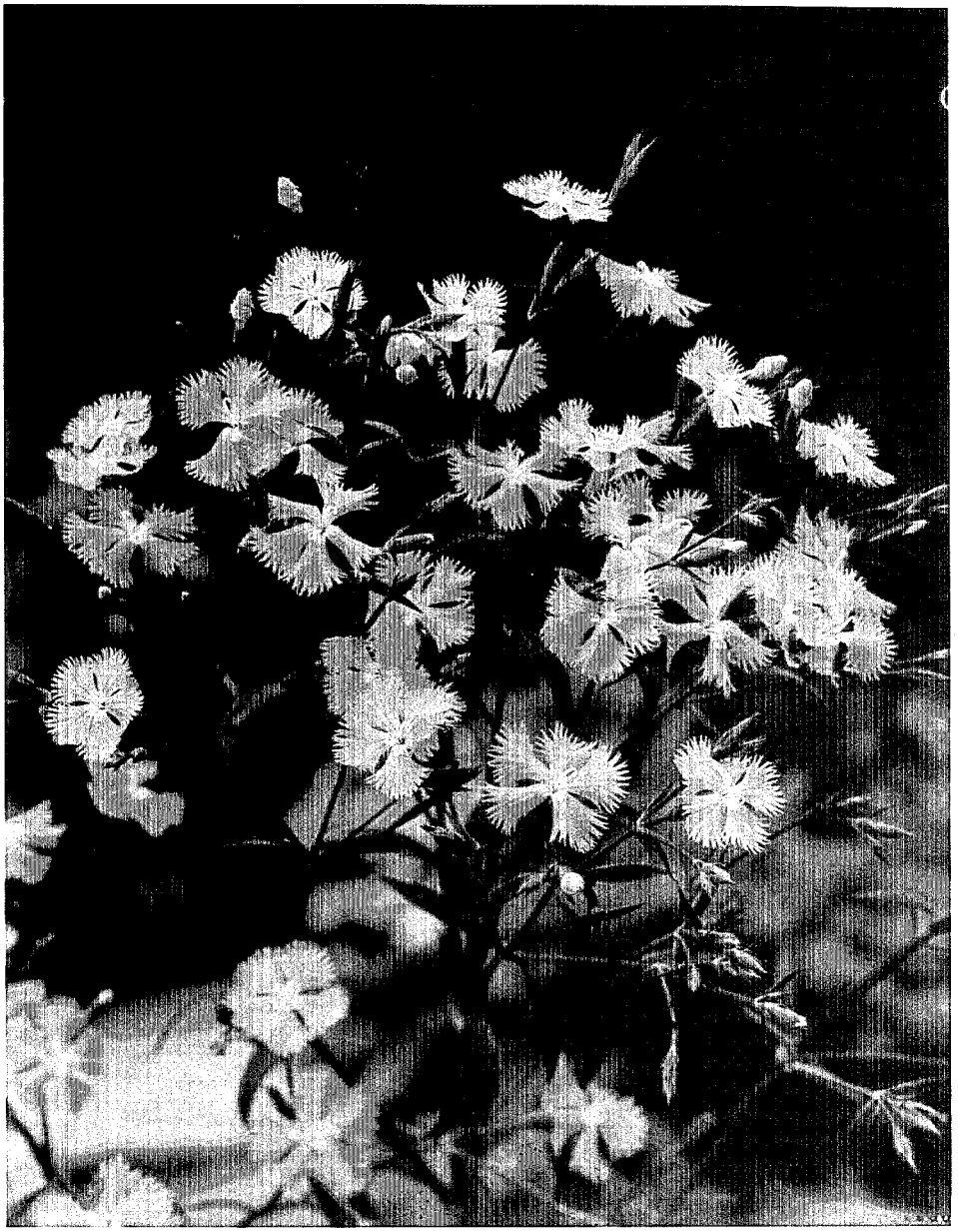

* * * * *